United States Patent
Sherriff et al.

(10) Patent No.: US 7,530,502 B2
(45) Date of Patent: May 12, 2009

(54) CLAMP FOR A RAIL TRANSDUCER

(75) Inventors: Brian Sherriff, Brackenfell (ZA); Francois Alvyn Burger, Windmeul (ZA)

(73) Assignee: Armscor Business (Proprietary) Limited (ZA)

( * ) Notice: Subject to any disclaimer, the term of this patent is extended or adjusted under 35 U.S.C. 154(b) by 10 days.

(21) Appl. No.: 10/555,506

(22) PCT Filed: May 6, 2004

(86) PCT No.: PCT/IB2004/001406

§ 371 (c)(1),
(2), (4) Date: Mar. 24, 2006

(87) PCT Pub. No.: WO2004/098974

PCT Pub. Date: Nov. 18, 2004

(65) Prior Publication Data

US 2006/0289666 A1    Dec. 28, 2006

(30) Foreign Application Priority Data

May 7, 2003   (ZA) ................................ 2003/3505

(51) Int. Cl.
*B61K 9/00*    (2006.01)
(52) U.S. Cl. .................. 238/338; 238/14.13; 238/14.14; 246/247; 246/249; 246/169 S; 246/169 D; 246/169 A; 246/169 R
(58) Field of Classification Search ............. 246/169 R, 246/169 A, 169 D, 169 S; 238/341, 378, 238/14.14, 338; 248/689, 70, 72, 229.11, 248/486, 229.21, 228.2, 231.31, 274.1, 316.2
See application file for complete search history.

(56) References Cited

U.S. PATENT DOCUMENTS

| | | | | |
|---|---|---|---|---|
| 3,147,822 A | * | 9/1964 | Watts | .......................... 184/3.1 |
| 3,564,488 A | * | 2/1971 | Higashi | ........................ 367/90 |
| 3,830,427 A | * | 8/1974 | Polidori | .................... 238/14.14 |
| 4,049,230 A | * | 9/1977 | Minniear | ..................... 248/539 |
| 6,371,417 B1 | * | 4/2002 | Southon | ...................... 246/247 |
| 6,431,794 B1 | * | 8/2002 | Zweber | ....................... 405/221 |

FOREIGN PATENT DOCUMENTS

| | | |
|---|---|---|
| EP | 0592031 A | 4/1994 |
| WO | WO00/17632 A | 3/2000 |
| WO | WO02/059593 A | 8/2002 |

OTHER PUBLICATIONS

Richard Reiff and Steve Renfrow, "Research Summary: Demonstration of an Acoustic Rail Break Detection System," May 2002, Transportation Technology Center, Inc., Association of American Railroads, Pueblo, Colorado.

* cited by examiner

*Primary Examiner*—Mark T Le
(74) *Attorney, Agent, or Firm*—Seyfarth Shaw LLP

(57) ABSTRACT

A clamp for securing a transducer to a train rail comprises a bracket having a base which engages the foot of the rail. An upright arm at one end of the base extends adjacent the web of the rail and carries a threaded adjuster which engages the transducer and urges it into contact with the rail. The clamp is sufficiently resilient so that, when the adjuster is tightened to a predetermined extent, both temporary and permanent deformation of the rail can be accommodated without difficulty.

6 Claims, 1 Drawing Sheet

CLAMP FOR A RAIL TRANSDUCER

This application is a U.S. National Phase of International Patent Application Ser. No. PCT/IB2004/001406, filed May 6, 2004 which claims priority to South African Patent Application No. 2003/3505 filed May 7, 2003.

BACKGROUND OF THE INVENTION

THIS invention relates to a clamp for securing a transducer to a train rail.

In order to monitor the condition of train rails, acoustic or ultrasonic transducers are used to excite a rail so that the resulting propagation modes travel for a substantial distance along the rail. A receiver unit located a substantial distance away from the transducer can detect such propagation modes and can be used to provide an indication of the condition of the rail, and can thus be used to warn of a break in the rail or other mechanical damage. A system of this kind is described in South African patent no. 99/6936.

In systems of the kind described above, it is important that the transducer used to excite the rail should be held in firm and consistent contact with the rail. This is made difficult by the fact that the passage of rolling stock over the rail causes temporary and eventually permanent distortion of the rail profile. Another practical consideration is the ease of mounting of the transducer, and the requirement that little or no damage be caused to the rail.

It is an object of the invention to provide a clamp for securing a transducer to a rail which addresses the above considerations.

SUMMARY OF THE INVENTION

According to the invention there is provided a clamp for securing a transducer to a train rail of the kind having a foot, a web, and a head, the clamp comprising:

a bracket having a base portion shaped to engage the foot of the rail and an upright arm at one end of the base portion which extends adjacent the web of the rail when the base portion engages the foot of the rail; and an adjuster supported by the arm for engaging the transducer and urging the transducer into contact with the rail.

The base portion of the bracket may be shaped to fit under the foot of the rail.

Preferably, the bracket is formed from a material selected to be sufficiently resilient to deform elastically when the adjuster urges the transducer into contact with the rail in use.

For example, the bracket may be formed from stainless steel.

The adjuster may comprise a threaded member passing through the arm and movable axially towards the rail on rotation thereof, the threaded member being oriented so as to urge the transducer into engagement with the rail between the head and the web of the rail.

In a preferred embodiment of the invention, the threaded member is an adjuster bolt which passes through an aperture in an upper end of the arm and a complementally threaded aperture in a reaction member located against the arm, between the arm and the rail, so that tightening of the adjuster bolt in use urges the transducer against the rail and causes elastic deformation of the arm away from the rail.

The reaction member may be a pin or bar supported by the arm with its axis parallel to the rail, the pin or bar being rotatable about its axis to an extent sufficient to allow the adjuster bolt to accommodate variations in the shape of the transducer and/or the rail.

The threaded member is preferably adjustable to apply force to the transducer on a line inclined at 45° to the plane of the rail web at the point of intersection of the rail head and the rail web.

The invention extends to a transducer installation comprising a clamp as defined above, and a transducer comprising a body shaped to be urged into engagement with a train rail between the head and foot of the rail.

DESCRIPTION OF AN EMBODIMENT

Figure 1:
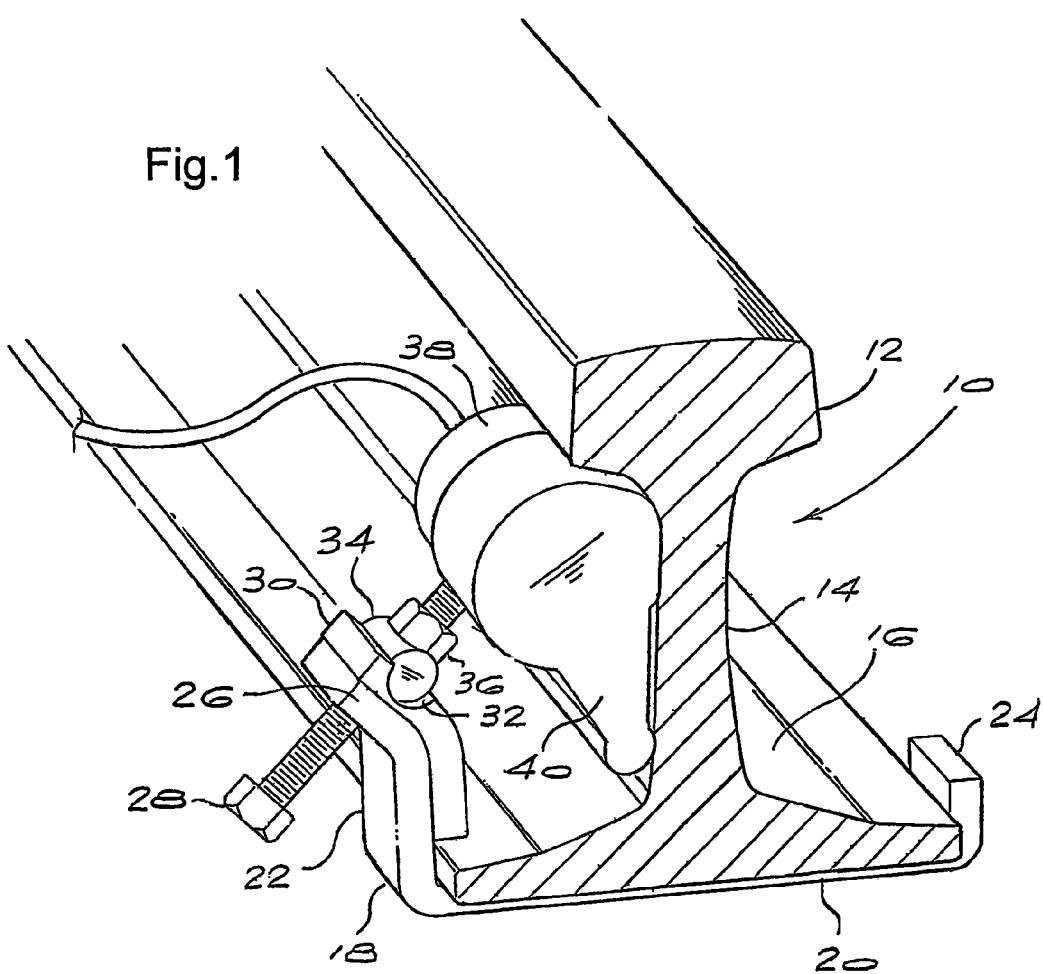
FIG. 1 is a pictorial view of a clamp according to the invention in use, clamping a transducer to a rail.
Figure 2:
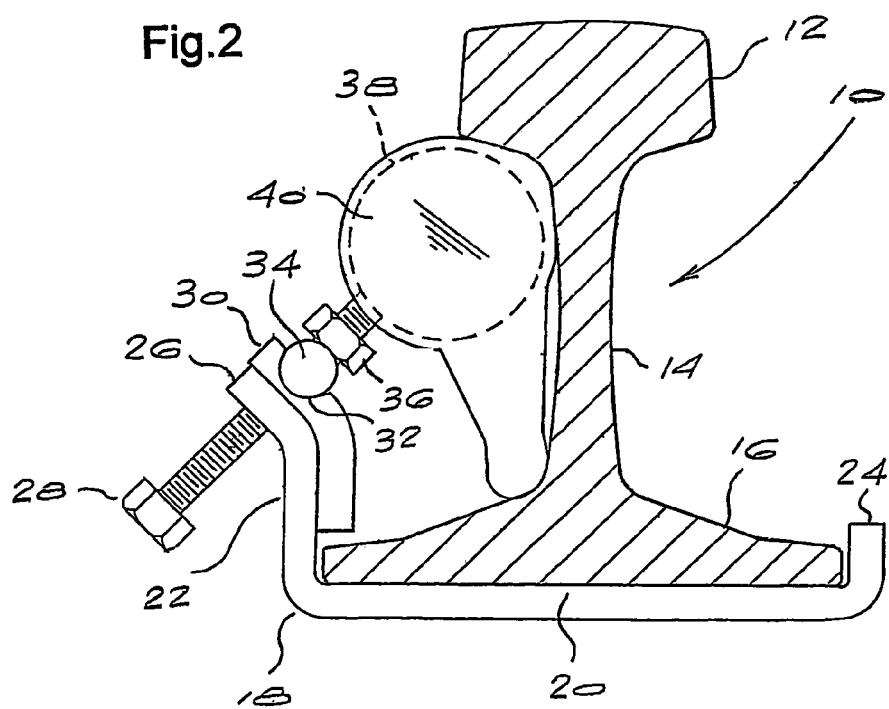
FIG. 2 is an end view of the clamp shown in FIG. 1.

Referring to the drawings, a steel train rail 10 forming part of a railway line is shown. The rail 10 comprises a head 12, an upright web 14 and a flattened foot 16.

Fitted under the foot of the rail is a bracket 18 forming part of a clamp of the invention, the bracket having a foot portion 20 which fits under the foot of the rail, and an upright arm 22 at one end of the foot portion. The bracket 18 is formed from a single piece of steel bar, the thickness of the bar and the type of steel being selected to provide the desired characteristics, particularly suitable resilience or springiness. For example, type 316 stainless steel is a suitable material, having excellent corrosion resistance, a high tensile strength to enable a high clamping force to be achieved, and a suitable degree of resilience or springiness to enable the necessary clamping force to be maintained, as described below. Another material having suitable resilience and mechanical properties could be used instead.

At the end of the foot portion 20 of the bracket remote from the arm 22, an upwardly extending flange 24 is provided. The bracket is retained between the underside of the foot 16 of the rail and a sleeper or other support on which the rail rests. Once the bracket 18 has been fitted to the underside of the rail, the flange 24 and the arm 22 prevent removal of the bracket from the rail, without additional fasteners being required. This has the advantage that no modification of the rail, whether by the drilling of holes into the rail or in any other way, is required.

The upper end 26 of the arm 22 is bent outwardly at approximately 45°, and an aperture is formed in the end 26 to accommodate a threaded adjuster bolt 28. On the side of the arm 22 closest to the rail 10, a mounting plate 30 shaped complementally to the upper end of the arm 22 and formed of stainless steel is mounted, for example by being welded to the arm 22. The aperture in the upper end 26 of the arm 22 also extends through the mounting plate 30, so that the bolt 28 is a loose fit in the aperture. A horizontal part-cylindrical groove 32 is formed in the upper surface of the mounting plate 30 and accommodates a stainless steel pin or bar 34 which is oriented with its longitudinal axis parallel to the axis of the rail 10. A transverse threaded hole is formed in the pin or bar to receive the bolt 28, so that rotation of the bolt about its axis moves its upper end towards (or away from) the rail. A nut 36 is fitted to the threaded inner end of the adjuster bolt to allow locking of the clamp once the bolt 28 has been adjusted to the required position.

The aperture in the upper end 26 of the arm and the corresponding aperture in the plate 30 are sufficiently large to permit the pin or bar 34 to be rotated about its axis in the groove 32, thus changing the angle of the bolt slightly relative to the plane of the rail web, to accommodate variations in the shape of the rail 10 or the transducer which is to be clamped against the rail in use.

A transducer 38 which comprises a stack of piezo-electric discs in a cylindrical housing, bolted at one end to an aluminium body 40 and having a back mass at the other end, is located against the upper part of the rail web and the underside of the rail head as shown, with the upper end of the adjuster bolt 28 bearing against the aluminium body 40 of the transducer. The aluminium body 40 is shaped to fit snugly against the web of the rail, abutting the portions of the rail between the underside of the head and the web, and between the web and the foot, as illustrated. When the transducer is correctly located against the rail, the bolt 28 can be swiveled to align it correctly, and then tightened to the required extent before being locked in position by tightening the nut 36.

When the adjuster bolt 28 is torqued sufficiently, for example, to a value in the region of 15 Nm, the arm 22 is deformed elastically away from the head and web of the rail, and the base portion of the bracket 18 underneath the foot of the rail is caused to bend or bow somewhat. This causes the aluminium body 40 of the transducer 38 to be urged resiliently against the rail, the arrangement being able to accommodate both temporary and permanent deformation of the rail in normal use, while maintaining a constant mating force at the interface between the transducer and the rail. The relatively soft aluminium body of the transducer can deform to accommodate such deformation of the rail, maintaining an adequate contact area between the transducer and the rail.

By providing an insulating bush at the interface between the transducer and the fastening bolt and an insulating sheet of suitable plastics material between the transducer and the rail, the transducer can readily be electrically isolated from the rail if required.

With the above described arrangement, the force line of the clamping arrangement is at 45° to the plane of the rail web at the point of intersection of the rail head and the web, ensuring optimum excitation signal insertion into the rail. This ensures that, within mechanical profile constraints, the rail is excited near its center of mass.

The axis of excitation in the transducer is along the central axis thereof. When the transducer is clamped to the rail, this results in asymmetric excitation relative to the center line of the rail. In other words, the excitation axis runs parallel to the rail center line at a standoff distance of roughly 45 mm for a typical rail. This results in the excitation of longitudinal waves (that is, along the center line of the rail) as well as flexural waves, and a number of other waves such as shear waves. The different modes, as viewed at a monitoring position located a substantial distance away from the excitation position, interfere with each other due to differing relative phase values at any specific point. The interference can be constructive or destructive, depending on the distance from the point of excitation, effectively resulting in complex modulation of the monitored wave. The magnitude of the excited modes, as well as the propagation loss experienced by the modes, is further influenced by rail temperature and related compression and stress forces. The excitation of different modes ensures that an adequate signal will be present at the monitoring position regardless of these factors, over distances in the region of 2 500 meters.

The invention claimed is:

1. A clamp for securing a transducer to a train rail of the kind having a foot, web, and a head, the clamp comprising:
   a bracket having a base portion shaped to engage the underside of the foot of the rail and including an integral retaining formation to prevent removal of the bracket from the rail, and an upright arm at one end of the base portion which extends adjacent the web of the rail when the base portion engages the foot of the rail; and
   an adjuster supported by the arm for engaging the transducer and urging the transducer into contact with the rail, the adjuster comprising a threaded member passing through the arm and movable axially towards the rail on rotation thereof, the threaded member being oriented so as to urge the transducer into engagement with the rail between the head and the web of the rail;
   wherein both the base portion and the upright arm of the bracket are formed from a material selected to be sufficiently resilient to deform elastically when the adjuster urges the transducer into contact with the rail in use, to accommodate both temporary and permanent deformation of the rail while applying a substantially constant force between the transducer and the rail in normal use.

2. A clamp according to claim 1 wherein the bracket is formed from stainless steel.

3. A clamp according to claim 1 wherein the threaded member is an adjuster bolt which passes through an aperture in an upper end of the arm and a complementally threaded aperture in a reaction member located against the arm, between the arm and the rail, so that tightening of the adjuster bolt in use urges the transducer against the rail and causes elastic deformation of the arm away from the rail.

4. A clamp according to claim 3 wherein the reaction member is a pin or bar supported by the arm with its axis parallel to the rail, the pin or bar being rotatable about its axis to an extent sufficient to allow the adjuster bolt to accommodate variations in the shape of the transducer and/or the rail.

5. A clamp according to claim 1 wherein the threaded member is adjustable to apply force to the transducer on a line inclined at 45° to the plane of the rail web at the point of intersection of the rail head the rail web.

6. A transducer installation comprising a clamp according to claim 1, and an acoustic or ultrasonic transducer comprising a body shaped to be urged into engagement with a train rail between the head and foot of the rail with a predetermined force by the clamp, thereby to transfer acoustic or ultrasonic energy between the transducer and the rail.

* * * * *